(12) United States Patent
Hong et al.

(10) Patent No.: US 9,795,306 B2
(45) Date of Patent: Oct. 24, 2017

(54) METHOD OF ESTIMATING BLOOD PRESSURE BASED ON IMAGE

(71) Applicant: Research and Business Foundation Sungkyunkwan University, Suwon-si (KR)

(72) Inventors: Kwang-Seok Hong, Gwacheon-si (KR); Ho Sung Lee, Incheon (KR); JinSoo Park, Gumi-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/204,133

(22) Filed: Jul. 7, 2016

(65) Prior Publication Data

US 2017/0007137 A1 Jan. 12, 2017

(30) Foreign Application Priority Data

Jul. 7, 2015 (KR) .................. 10-2015-0096470

(51) Int. Cl.
| | |
|---|---|
| *A61B 5/02* | (2006.01) |
| *A61B 5/021* | (2006.01) |
| *A61B 5/00* | (2006.01) |
| *A61B 5/103* | (2006.01) |

(52) U.S. Cl.
CPC ........ *A61B 5/02125* (2013.01); *A61B 5/0077* (2013.01); *A61B 5/1032* (2013.01); *A61B 5/7203* (2013.01); *A61B 5/725* (2013.01); *A61B 5/7278* (2013.01)

(58) Field of Classification Search
None
See application file for complete search history.

(56) References Cited

U.S. PATENT DOCUMENTS

| | | | |
|---|---|---|---|
| 2014/0012142 A1* | 1/2014 | Mestha ................ | A61B 5/0075 600/480 |
| 2014/0073969 A1* | 3/2014 | Zou ..................... | A61B 5/02108 600/479 |
| 2014/0276104 A1* | 9/2014 | Tao ...................... | A61B 5/7239 600/476 |
| 2014/0343393 A1* | 11/2014 | Lee .......................... | H01Q 1/36 600/407 |

* cited by examiner

*Primary Examiner* — Brian T Gedeon
*Assistant Examiner* — Ankit D Tejani
(74) *Attorney, Agent, or Firm* — NSIP Law

(57) ABSTRACT

A method of estimating a blood pressure based on an image is provided. The method includes obtaining, by camera, an image including a skin of a user, determining, by a computer device, a skin region, in which at least one portion of the skin is displayed, from the image, and storing a mean value of color data of a designated color model for each of two target regions which have different positions in the skin region from each other, estimating, by the computer device, a pulse-wave transit time (PTT) based on a pulse wave signal determined based on a change in the mean value of the color data for each of the two target regions, and estimating, by the computer device, the blood pressure using the PTT.

10 Claims, 6 Drawing Sheets

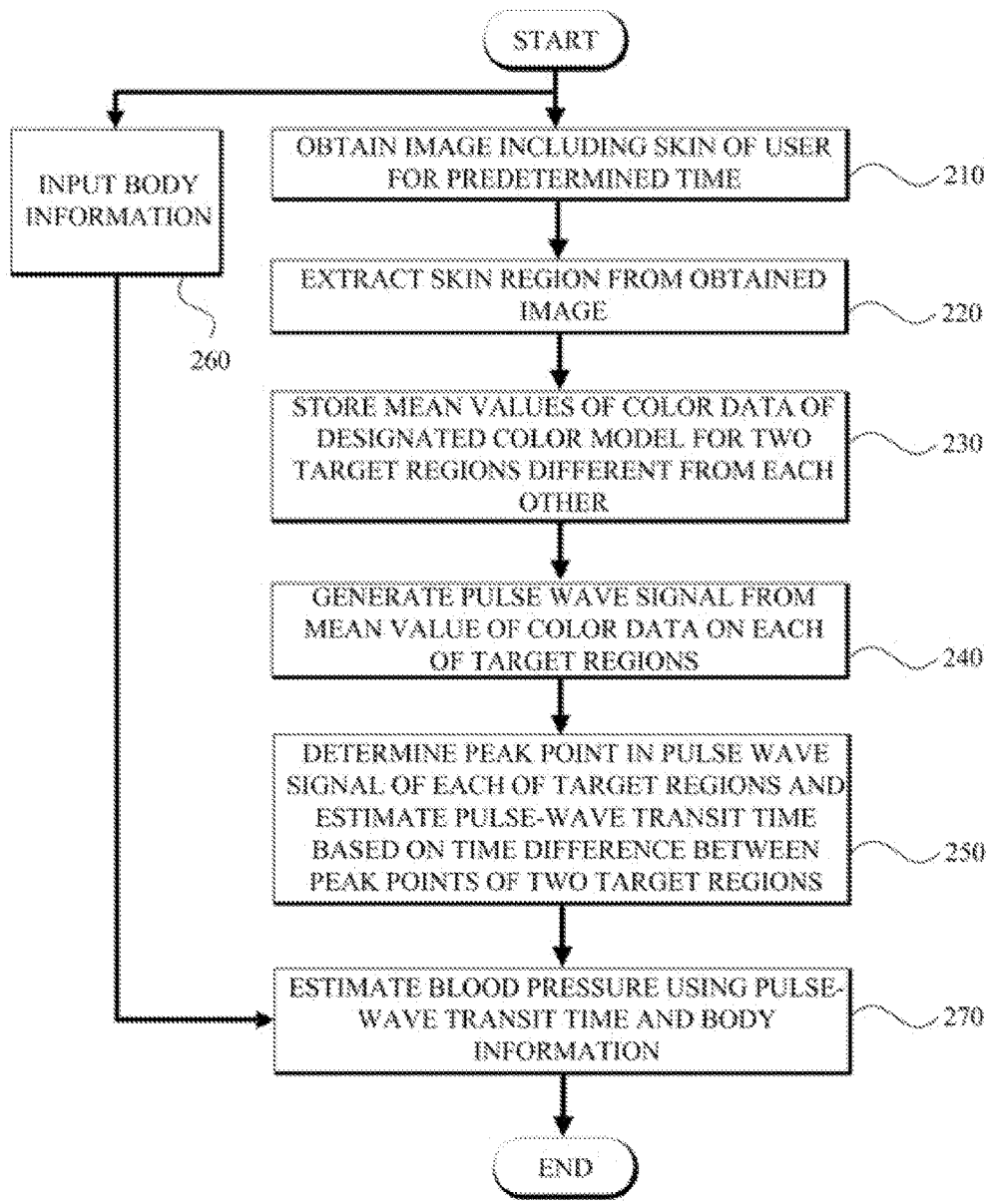

METHOD OF ESTIMATING BLOOD PRESSURE BASED ON IMAGE

CROSS-REFERENCE TO RELATED APPLICATION

This application claims the benefit under 35 USC 119(a) of Korean Patent Application No. 10-2015-0096470 filed on Jul. 7, 2015, in the Korean Intellectual Property Office, the entire disclosure of which is incorporated herein by reference for all purposes.

BACKGROUND

1. Field of the Invention

The following description relates to a method of estimating a blood pressure of a person.

2. Discussion of Related Art

A blood pressure is measured by applying a pressure to an upper arm of a subject after attaching a cuff to the upper arm of the subject.

A method of estimating a blood pressure using a photo-plethysmography (PPG) signal and an electrocardiogram (ECG) signal is developed. The method estimates a blood pressure based on a pulse wave transmission rate which is calculated by the PPG signal and the ECG signal.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a method of estimating a blood pressure based on an image including obtaining, by camera, an image including a skin of a user, determining, by a computer device, a skin region, in which at least one portion of the skin is displayed, from the image, and storing a mean value of color data of a designated color model for each of two target regions which have different positions in the skin region for a period of time, estimating, by the computer device, a pulse-wave transit time (PTT) based on a pulse wave signal determined based on a change in the mean value of the color data for each of the two target regions, and estimating, by the computer device, the blood pressure using the PTT.

BRIEF DESCRIPTION OF THE DRAWINGS

FIG. 2 illustrates an example of a flowchart for describing a method of estimating a blood pressure using a video.

Figure 1:
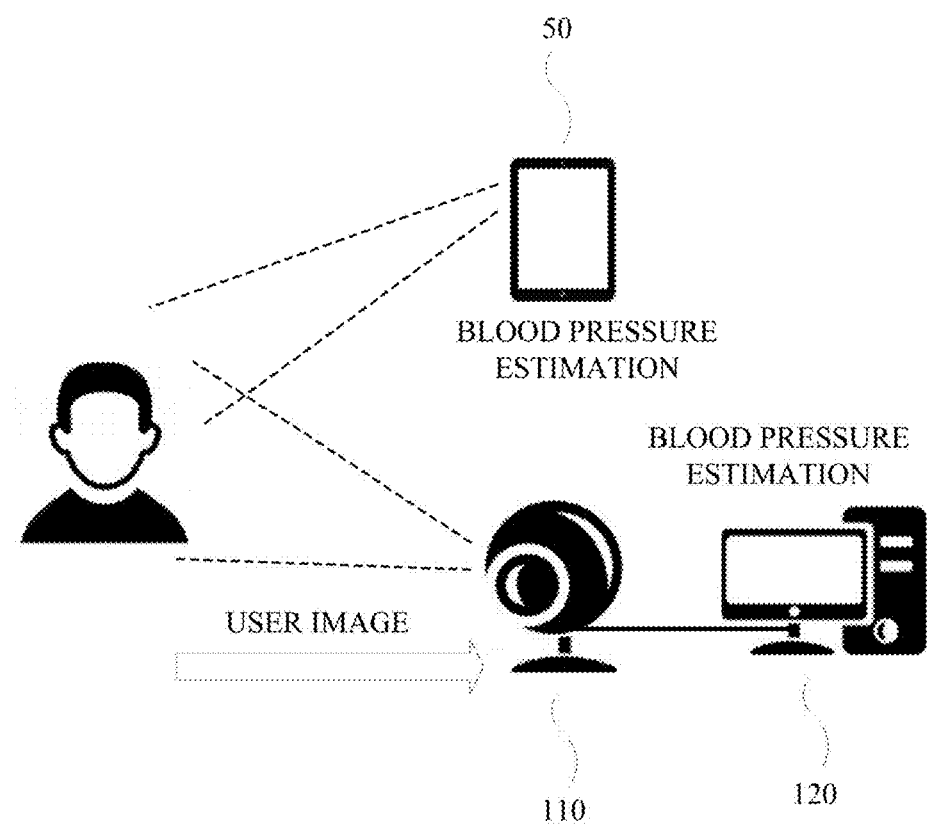
FIG. 1 illustrates an example of a system for estimating a blood pressure using a video.

Throughout the drawings and the detailed description, unless otherwise described, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION OF EXEMPLARY EMBODIMENTS

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

All terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It should also be noted that in performing a method or an operating method, processes of the method may occur out of noted order unlike otherwise mentioned. In other words, the respective processes may be executed in the same order as the noted order, may be executed substantially concurrently, or may be executed in the reverse order.

A technique described herein may be a method of estimating a blood pressure based on an image of a user. A conventional method using a photo-plethysmography (PPG) signal and an electrocardiogram (ECG) signal estimates a blood pressure using a pulse-wave transit time (PTT). However, the conventional method using the PPG signal and the ECG signal measures the PPG signal and the ECG signal through a separate sensor device and estimates the PTT based on the measured PPG signal and ECG signal. A technique described herein may estimate a PTT based on a video of a user, and estimate a blood pressure based on the PTT.

FIG. 1 illustrates an example of a system for estimating a blood pressure using a video. In FIG. 1, two devices are illustrated. One device is a smart device 50. Generally, devices, such as a smart phone, a tablet personal computer (PC), etc., include a camera and a processor capable of processing a predetermined image and data. Accordingly, a user image may be obtained through the smart device 50, and a PTT may be estimated by processing the obtained user image using a predetermined process. Further, a separate camera 110 may obtain the user image, and a computer device 120 may receive the user image obtained by the camera 110 and estimate the PTT. The smart device 50 corresponds to a device including both a camera and a computer device. Further, a video of the user may be obtained by the separate camera 110, and the computer device 120 located in a remote place may receive the video through a storage medium, such as a secure digital (SD) memory card, or a network. The configuration of the system for estimating a blood pressure may be diverse. A method of estimating a blood pressure based on an image which will be described hereinafter may be implemented by only using a tool for obtaining an image of a user and a computer device for processing the obtained image.

FIG. 2 illustrates an example of a flowchart for describing a method of estimating a blood pressure using a video.

First, an image of a user is obtained by a camera (S210). The camera obtains the image during a predetermined time. Although described hereinafter, this is because a change degree of a mean value of color data of a designated color model in the image has to be extracted. In this case, a skin of the user should be included in the image of the user. For example, the camera may photograph a region which includes the skin of the user such as a face, arms, hands, etc. After this, the computer device extracts a skin region from the image (S220). The skin region refers to a region in which the skin is displayed in the image. For example, only a facial region may be extracted by removing a background from the image using a face recognition algorithm. The computer device may extract the skin region from the image using a facial region detection algorithm or a skin detection algorithm. The computer device refers to a device including a smart device having a camera, a PC connected to a camera, a computer device located in a remote place and receiving an image collected by a camera, a server receiving an image collected by a camera, etc.

The computer device continuously stores mean value of color data of a designated color model for two target regions in the skin region (S230) for a period of time. Operation S230 includes an operation of setting the two target regions and an operation of storing a mean value of the color data for each target region. The computer device sets the two target regions in the skin region.

When the computer device extracts one continuous skin region, the computer device may divide the one continuous skin region into two or set two specific regions in the one continuous skin region as the two target regions. For example, when the skin region is a facial region, the computer device may set the two target regions by dividing the facial region into two. Further, when images of the user are obtained using two cameras, the computer device may extract the skin region from the image obtained by each camera and also set the two skin regions as the target regions. For example, when one camera photographs a facial region and the other camera photographs a hand region, the computer device may also set the facial region and the hand region as the target regions.

The computer device continuously stores the mean value of the color data of the designated color model for the two target regions for a period of time. A color of the skin is changed according to a blood flow flowing in a blood vessel adjacent to the skin. That is, a blood flow with a regular rule may be determined by monitoring the mean value of the color data for the target regions. The regular rule refers to a blood flow moving according to a heartbeat. (1) The computer device may calculate the mean value of the color data of the target regions for each frame and store the mean value of the color data of each frame. In this case, the computer device may store the mean value of the color data in units of frames. (2) Further, the computer device may also calculate and continuously store the mean value of the color data for a frame at predetermined intervals. In this case, the computer device calculates the mean value of the color data of the designated color model for a still frame at predetermined intervals. (3) Moreover, the computer device may also calculate and continuously store the mean value of all color data of the frame in units of predetermined frames.

The computer device stores the mean value of the color data of the designated color model of the two target regions for a period of time and generate a pulse wave signal (S240). As described above, the mean value of the color data of the target regions are associated with a blood flow. In a graph in which a vertical axis represents the mean value of the color data and a horizontal axis represents time, a change in a value calculated by the mean value of the color data may be a signal having a predetermined waveform. The computer device may convert the mean value of the color data of the designated color model into a pulse wave signal using a band pass filter. Further, the computer device may also use another filter for removing noise from the pulse wave signal.

The computer device determines associated peak points from pulse wave signals for the two target regions and estimates a time difference between two peak points as a PTT (S250). There may be a plurality of peak points in one pulse wave signal. The peak point is a point where a value of the pulse wave signal calculated by applying the band pass filter to the mean value of the color data of the designated color model is increased. The mean value of the color data may be changed according to the blood flow.

When a heart beats once, a constant amount of blood flow is transmitted to an artery, and then, the amount of blood flow is decreased for a moment. This operation may be repeated according to the heartbeat. When the heart beats, an operational pattern in which the amount of blood flow or a speed of the blood flow is increased and decreased according to the heartbeat is repeated even in a blood vessel connected along an artery. As a result, a point where a value of the pulse wave signal calculated by applying the band pass filter to the mean value of the color data of the designated color model in the target region is increased is attributable to an operation in which the heart pushes the blood flow in the artery. Accordingly, the peak points in the pulse wave signal may regularly or somewhat irregularly appear according to the heartbeat.

The computer device finds the peak points in the two target regions. In this case, the peak points found in the two target regions are peak points associated with each other. The associated peak points refer to points influenced by a specific heartbeat. For example, when the heart beats once, the amount of blood flow is first increased in a blood vessel located at a first point close to the heart, and is then increased in a blood vessel located at a second point which is a predetermined distance away from a blood vessel extending from the first point. The amount of blood flow is increased at the two peak points having times different from each other according to the same heartbeat. In the change in the amount of blood flow according to the same heartbeat, a time interval in which the change occurs is changed according to a distance between the two peak points. The peak points associated with each other in the two target regions is attributable to a change in the amount of blood flow according to the same heartbeat. Accordingly, the computer device finds the associated peak points by considering a distance between the target regions. The computer device may estimate the PTT based on the time interval between the associated peak points.

Finally, the computer device may estimate a blood pressure using the PTT (S270). An equation used for the blood pressure estimation may be an equation used in the technology using the PPG signal and the ECG signal. Generally, the blood pressure is estimated using a regression equation. The equation used for estimating the blood pressure includes body information of the user in addition to the PTT. Accordingly, the computer device has to receive the body information from the user in advance or receive body information of a corresponding user from a database storing the body information (S260). The body information includes age, height, weight, etc. of the user.

Figure 3A:
FIGS. 3A-3D illustrate an example of extracting a facial image and determining two target regions.
Figure 3B:
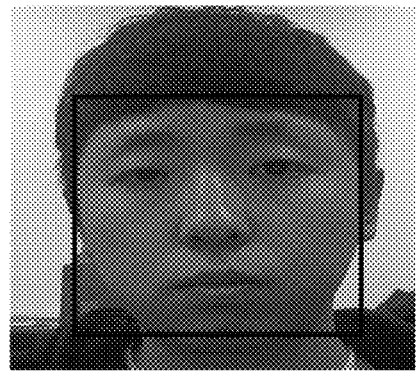
Figure 3C:
Figure 3D:
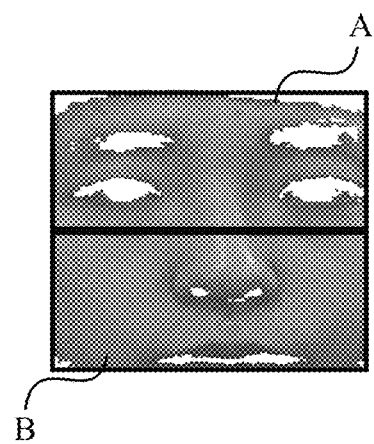

FIG. 3A to FIG. 3D illustrate an example of extracting a facial image and determining two target regions. FIG. 3A to FIG. 3D illustrate an example in which the skin region is the facial region. FIG. 3A illustrates an example in which an image including a face of a user is obtained by one camera. FIG. 3B illustrates an example in which the computer device recognizes a facial region from the image obtained by the camera using a facial region recognition algorithm. The facial region refers to a region in which a portion covered by hair or various clothes is excluded and the skin is exposed outside. In FIG. 3B, a region represented by a rectangular shape is the facial region recognized by the computer device. Various algorithms may be used for facial region recognition. FIG. 3C illustrates an example of extracting a skin region from the recognized facial region. FIG. 3D illustrates an example of dividing the recognized facial region into an upper region A and a lower region B. The upper region A and the lower region B corresponds to the two target regions. The facial region is not necessarily divided to be equal. Further, the facial region is not divided, and two specific regions in the facial region may be set as the target regions.

Figure 4A:
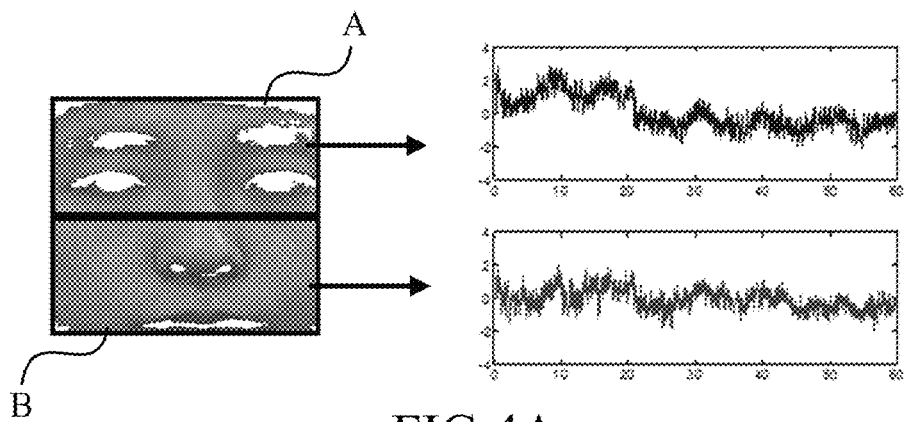
FIGS. 4A-4C illustrate an example of a diagram illustrating an operation of estimating a pulse-wave transit time (PTT) using a facial image.
Figure 4B:
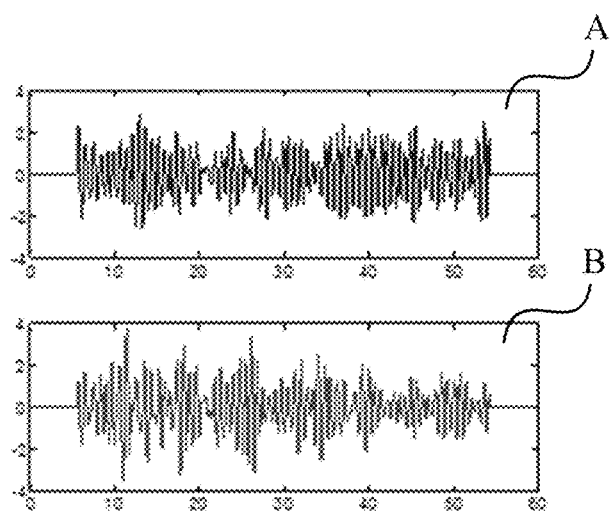
Figure 4C:
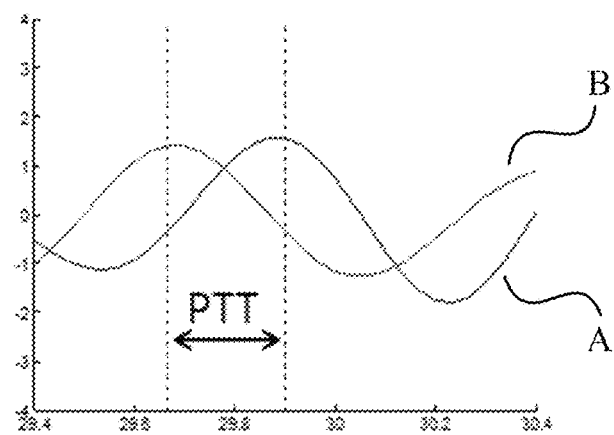

FIG. 4A to FIG. 4C illustrate an example of a diagram illustrating an operation of estimating a pulse-wave transit time (PTT) using a facial image. FIG. 4A illustrates values calculated by mean value of color data of a designated color model of two target regions in a signal form. The upper region A and the lower region B shown in FIG. 3D are illustrated as an example of the target regions.

FIG. 4A illustrates, as a graph, numerical values for the mean value of the color data for an entire frame obtained by calculating the mean value of the color data of the designated color model for each frame of a video obtained by capturing the target regions. The color data based on values of R, G, and B in a color image may be used. Alternatively, the mean value of the color data may be determined using another color model (YUV, YCbCr, YCgCo, etc.) converted from an RGB image.

FIG. 4B illustrates an example of converting the mean value of the color data of the designated color model of the target regions shown in FIG. 4A into a pulse wave signal.

FIG. 4A illustrates signals corresponding to change of signals calculated by the mean value of the color data stored for each frame. The signals calculated by the mean value of the color data of the target regions include a pulse wave signal of a photographed target and noise according to a movement generated with the pulse wave signal. A filtering operation is needed to remove the noise. A filter may be a band pass filter which passes only a frequency of a corresponding region to extract only a pulse wave signal component. FIG. 4B is an example of extracting only signals corresponding to the pulse waves from the signals obtained by the mean value of the color data of the target regions.

FIG. 4C illustrates an example of estimating a PTT between the two target regions (A and B) from the pulse wave signals. As described above, the pulse wave signals of the two target regions repeat a flow of increasing and decreasing with a constant period. Peak points associated with each other are found in the two target regions. In FIG. 4C, the peak points associated with each other in the two pulse wave signals are illustrated in a dotted line. When finding the peak point of each period from the two pulse wave signals, as shown in FIG. 4C, a time difference between the peak points of the two pulse wave signals is determined as the PTT. The PTT is not necessarily obtained based on the peak points between the two pulse wave signals. The PTT may be obtained based on other points since the PTT corresponds to the time difference between the two pulse wave signals.

Figure 5B:
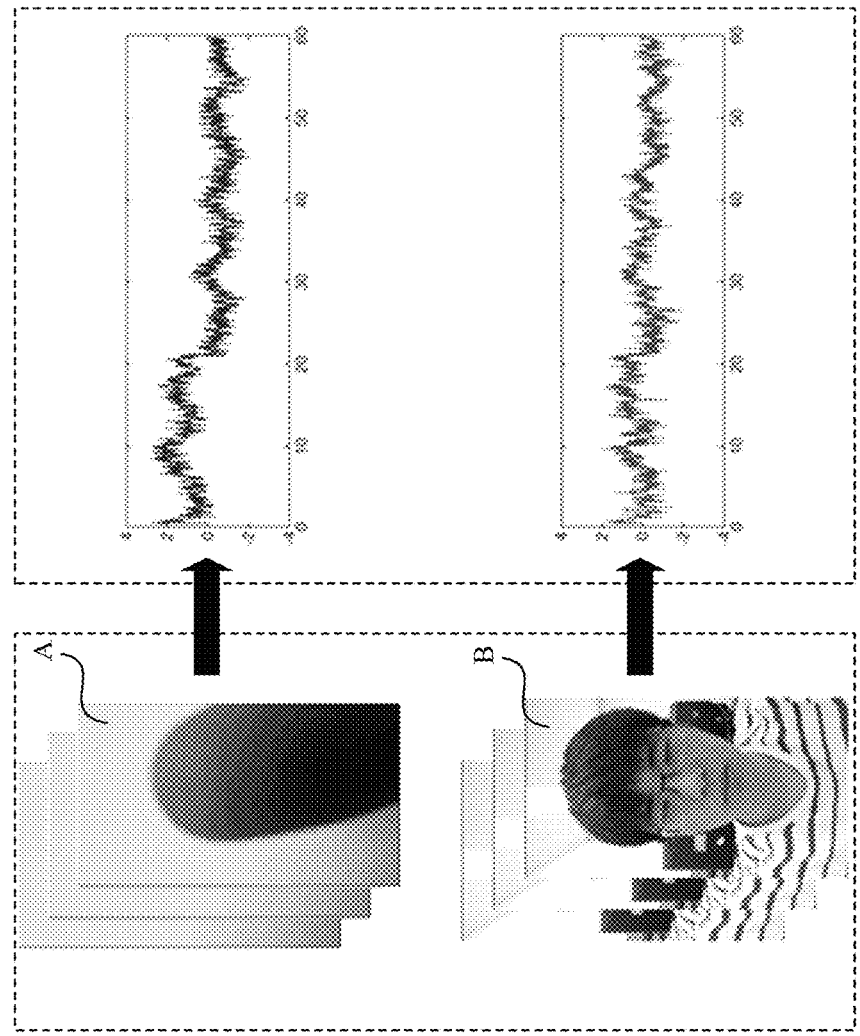
FIGS. 5A-5B illustrate an example of extracting change on mean value of color data of a designated color model on two target regions using a plurality of cameras.
Figure 5A:

FIG. 5A and FIG. 5B illustrate an example of extracting change on mean value of color data of a designated color model on two target regions using a plurality of cameras. FIG. 5A illustrates an example in which a user captures images using a front camera and a rear camera of a smart phone. The front camera obtains a facial image B of the user, and the rear camera obtains a finger image A of the user. FIG. 5B illustrates the mean value of the color data calculated based on each of the finger image A and the facial image B.

Subsequent operations are the same as described with reference to FIG. 4B and FIG. 4C. That is, the pulse wave signals may be calculated based on change in the mean value of the color data on the finger image A and the facial image B, and a PTT may be estimated from the two pulse wave signals.

When using two cameras as shown in FIG. 5A, basic brightness obtained by the two cameras may be different according to an environment in which images are obtained. In this case, it is preferable that the brightness be corrected in a process of processing the images, or two values be corrected in a predetermined level in a process of generating a change in a mean value of color data.

As described above, the computer device receives body information of a user before estimating a blood pressure. The body information includes age, height, weight, etc. Relation equations for calculating the blood pressure using the body information and the PTT are represented by the following Equations 1 and 2. Equation 1 is an equation representing a maximum blood pressure $P_s$, and Equation 2 is an equation representing a minimum blood pressure $P_d$.

$$P_s = b_{s0} + b_{s1} \times A + b_{s2} \times H + b_{s3} \times W + b_{s4} \times \ln\left(\frac{1}{T_{ptt}^2}\right) \quad \text{[Equation 1]}$$

$$P_d = b_{d0} + b_{d1} \times A + b_{d2} \times H + b_{d3} \times W + b_{d4} \times \ln\left(\frac{1}{T_{ptt}^2}\right) \quad \text{[Equation 2]}$$

In Equations 1 and 2, A represents age, H represents a height, W represents a weight, and $T_{ptt}$ represents a PTT. Constant values $b_{s0}$ to $b_{s4}$ and $b_{d0}$ to $b_{d4}$ used in Equations 1 and 2 may be obtained by a multiple regression analysis based on data information which is obtained in advance. The regression analysis is a method for estimating a value of a dependent variable corresponding to a constant value of an independent variable. Since the objective of the present invention is to estimate a blood pressure, a regression model is obtained by using the blood pressure as the dependent variable and the PTT or the age, the height, the weight, and the like needed for obtaining the blood pressure as the independent variables. When the regression model is obtained through a pre-test and information such as the PTT, the weight, and the height is obtained by using the operation described above, a blood pressure of a subject may be estimated.

Figure 6:
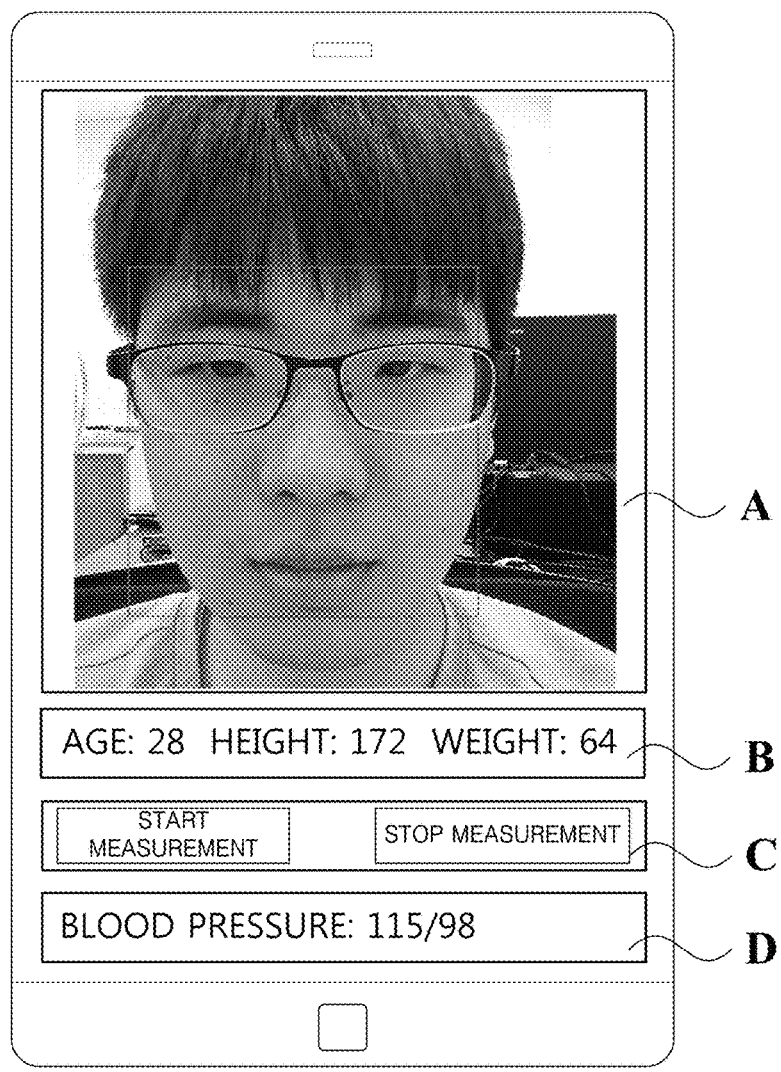
FIG. 6 illustrates an example of a screen measuring a blood pressure using a video in a smart phone.

FIG. 6 illustrates an example of a screen measuring a blood pressure using a video in a smart phone. FIG. 6 illustrates an example of the front of a smart phone. In a screen of the smart phone, a region represented by A represents an image which is currently being obtained by a camera. In the screen of the smart phone, a region represented by B is a screen through which body information of a user is input to estimate a blood pressure. In the screen of the smart phone, a region represented by C is a screen on which a menu for measuring a blood pressure is displayed. For example, when the user clicks a "start measurement" button after inputting body information of the user, a video is captured for a predetermined time, and a measured result value is displayed. A "stop measurement" button is a menu for temporarily stopping the measurement after starting the measurement. In the screen of the smart phone, a region represented by D is an example of displaying a result of the measured blood pressure based on the image.

According to the above-described embodiments of the example, since the blood pressure is estimated only using the video obtained by capturing the subject for the predetermined time, inconvenience of the subject can be reduced, and the blood pressure can be easily estimated.

The units described herein may be implemented using hardware components such as, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The media may also include, alone or in combination with the software program instructions, data files, data structures, and the like. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein. While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of estimating a blood pressure based on a video of a user, comprising:
    obtaining, by camera, an image including a skin of the user;
    determining, by a computer device, a skin region, in which at least one portion of the skin is displayed, from the image, and storing a specific value generated from color data of a designated color model for each of two different portions of the skin;
    estimating, by the computer device, a pulse wave signal based on a change in specific value of color data for each of the two different portions of the skin;
    estimating, by the computer device, a pulse-wave transit time (PTT) based on a time difference between local extrema of the pulse wave signals from the two different portions of skin; and
    estimating, by the computer device, the blood pressure using the PTT.

2. The method of claim 1, wherein the storing of the specific value comprises:
    dividing the skin region in the image into two and storing the specific value of the color data for the two different portions of the skin; or extracting skin regions from images obtained by two cameras respectively and storing the specific value of the color data by determining the extracted two skin regions as the two different portions of the skin.

3. The method of claim 1, wherein the storing of the specific value comprises:

setting, by the computer device, the two different portions of the skin by dividing the image; and generating a change in the specific value of the color data for each of the two different portions of the skin.

4. The method of claim 1, wherein:

the obtaining of the image comprises obtaining, by the camera, an image including a facial region of the user; and the storing of the specific value comprises extracting, by the computer device, the facial region from the image and classifying the facial region as two target different portions to be the two different portions of the skin.

5. The method of claim 1, wherein the storing of the specific value comprises storing, by the computer device, the specific value of the color data of the portions of the skin in units of frames or frames of a reference interval.

6. The method of claim 1, wherein the estimating of the PTT comprises generating, by the computer device, pulse wave signals for the portions of the skin from the change in the specific value of the color data using a band pass filter.

7. The method of claim 1, wherein the estimating of the PTT further comprises determining two associated peak points from the pulse wave signals for the respective target regions and estimates the PTT based on a time difference between the two peak points.

8. The method of claim 1, wherein the estimating the blood pressure comprises applying the PTT to an equation which is provided in advance through a multiple regression analysis and estimates the blood pressure.

9. The method of claim 1, further comprising before the estimating of the blood pressure, receiving age, height, and weight of the user, and applying the age, the height, the weight, and the PTT to an equation which is provided in advance through a multiple regression analysis.

10. The method of claim 1, wherein the specific value generated from color date is a mean value of the color data.

* * * * *